United States Patent [19]

Burkhardt et al.

[11] 4,276,425

[45] Jun. 30, 1981

[54] PROCESS FOR PREPARING CYCLIC DIMETHYLPOLYSILOXANES

[75] Inventors: Jürgen Burkhardt, Winhöring; Eckhart Louis, Burghausen, both of Fed. Rep. of Germany

[73] Assignee: Wacker-Chemie GmbH, Munich, Fed. Rep. of Germany

[21] Appl. No.: 56,485

[22] Filed: Jul. 11, 1979

[30] Foreign Application Priority Data

Dec. 9, 1978 [DE] Fed. Rep. of Germany ....... 2839652

[51] Int. Cl.³ ............................................... C07F 7/08
[52] U.S. Cl. ................................................... 556/460
[58] Field of Search .................. 260/448.2 E; 556/460

[56] References Cited

FOREIGN PATENT DOCUMENTS 843273  8/1960  United Kingdom ...................... 556/460
125252  9/1951  U.S.S.R. .................................. 556/460
469704  7/1975  U.S.S.R. .................................. 556/460

OTHER PUBLICATIONS

Noll, "Chemistry and Technology of Silicones," Academic Press, New York, (1968), p. 235.

Primary Examiner—Paul F. Shaver

[57] ABSTRACT

Cyclic dimethylpolysiloxanes are prepared by heating a mixture containing linear or branched organopolysiloxanes consisting of at least 50 mol percent dimethylsiloxane units and aqueous sulfuric acid in which the aqueous sulfuric acid contains from 50 to 85 percent by weight of sulfuric acid, while simultaneously recovering the cyclic dimethylpolysiloxanes thus formed.

3 Claims, No Drawings

PROCESS FOR PREPARING CYCLIC DIMETHYLPOLYSILOXANES

This invention relates to a process for preparing organopolysiloxanes and more particularly to a process for preparing cyclic dimethylpolysiloxanes from higher molecular weight linear or branched dimethylpolysiloxanes.

BACKGROUND OF INVENTION

High molecular weight organopolysiloxanes, such as gums and elastomers which were prematurely or partially cured have been discarded as waste materials. Since these materials are relatively expensive, it would be desirable to convert these materials to a form in which they could be utilized.

It is known that waste materials, such as high molecular weight organopolysiloxanes and gums which have been prematurely or partially cured as well as elastomers which are based on linear organopolysiloxanes may be converted to cyclic organopolysiloxanes. According to U.S. Pat. No. 2,934,550 to Jack, cyclic dimethylpolysiloxanes can be prepared by heating a mixture consisting essentially of linear organopolysiloxanes in the presence of catalysts such as aluminum or phosphous halides, which promote the redistribution of siloxane bonds at a temperature of at least 250° C. under essentially anhydrous conditions, while simultaneously distilling off cyclic organopolysiloxanes formed during the heating process.

Compared to the known process for preparing cyclic dimethylsiloxanes from essentially linear dimethylpolysiloxanes and compared to similar processes known for the utilization of waste materials containing linear or branched organopolysiloxanes comprising at least 50 mol percent of dimethylsiloxane units (U.S. Pat. No. 2,673,843, to Humphrey, et al and British Pat. No. 752,860,) the process of this invention has certain advantages. For example, it can be carried out at lower temperatures and it does not require anhydrous conditions. Moreover, it does not necessitate the separation of the catalyst which promotes the redistribution of siloxane bonds, during the distillation of the cyclic dimethylpolysiloxanes. Furthermore, the process of this invention produces higher yields of cyclic dimethylpolysiloxanes than was obtained heretofore in the same size equipment and in a shorter period of time.

Therefore it is an object of this invention to provide a process for preparing cyclic dimethylpolysiloxanes. Another object of this invention is to provide a process for preparing cyclic dimethylpolysiloxanes from high molecular weight organopolysiloxanes and elastomers. Still another object of this invention is to provide a process for preparing cyclic dimethylpolysiloxanes from waste materials containing organopolysiloxanes, gums or elastomers which have prematurely or partially cured. A further object of this invention is to provide a process for preparing cyclic dimethylpolysiloxanes from siloxane containing waste materials at lower temperatures and in greater yields.

SUMMARY OF INVENTION

The foregoing objects and others which will be apparent from the following description are accomplished in accordance with this invention, generally speaking, by providing a process for preparing cyclic dimethylpolysiloxanes which comprises heating a mixture of linear or branched organopolysiloxanes containing at least 50 mol percent of dimethylsiloxane units in the presence of aqueous sulfuric acid containing from 50 to 85 percent by weight of sulfuric acid, while simultaneously recovering the cyclic dimethylpolysiloxanes thus formed.

DETAILED DESCRIPTION OF INVENTION

In the process of this invention for preparing cyclic dimethylpolysiloxanes, it is possible to use all linear or branched organopolysiloxanes containing at least 50 mol percent of dimethylsiloxane units which could have been used heretofore in the preparation of cyclic dimethylpolysiloxanes by heating the organopolysiloxanes together with a catalyst which promotes the redistribution of siloxane bonds.

It is preferred that linear or essentially linear organopolysiloxanes which consist essentially of diorganosiloxane units and whose organic groups consist of at least 95 mol percent of methyl radicals be used in the process of this invention. Other organic groups which may be present in addition to the methyl radicals in the organopolysiloxanes used in this invention, are preferably ethyl, vinyl and/or phenyl groups. Siloxane units which may be present in addition to the diorganosiloxane units are preferably triorganosiloxane units, monoorganosiloxane units and $SiO_{4/2}$ units.

The organopolysiloxanes used in the process of this invention may for example be present in the form of compositions which are capable of being cross-linked to form elastomers or which are partially or fully cross-linked and which in addition to the cross-linkable organopolysiloxanes contain such additives as are generally used in the preparation of elastomers, for example fillers, pigments, cross-linking catalysts or catalyst residues. The organopolysiloxanes used in the process of this invention may also be present in the form of oils which in addition to the linear organopolysiloxanes may contain other substances such as, for example parafffin wax. Compositions such as described above or elastomers consisting of such compositions are obtained as waste materials, for example during the processing of diorganopolysilocane-based compositions which can be cross-linked by the formation of radicals, due to molding and cross-linking under pressure. Waste materials which consist essentially of oily, linear, organopolysiloxanes are generated in treating or coating textiles.

Also, mixtures of various types of organopolysiloxanes and of course various types of organopolysiloxane waste materials may be used in the process of this invention. It is, for example, possible to use waste materials containing organopolysiloxane elastomers and organopolysiloxane oils.

The aqueous sulfuric acid which contains from 50 to 85 percent by weight of sulfuric acid, has a density of $D^{20} = 1.40$ to $178$ g/cm$^3$.

If the sulfuric acid content of the aqueous sulfuric acid is less than 50 percent by weight, based on the total weight of the sufuric acid and water, then the formation of the cyclic dimethylpolysiloxane requires a longer period of time than is desirable. Conversely, if the sulfuric acid content of the aqueous sulfuric acid is in excess of 85 percent by weight, based on the total weight of the sulfuric acid and water, then the organopolysiloxanes are too easily carbonized.

It is preferred that the aqueous sulfuric acid catalyst used in the process of this invention to promote the redistribution of siloxane bonds, consist of from 55 to 80 percent by weight of sulfuric acid, which corresponds to a density of $D^{20}=1.45$ to 1.73 g/cm$^3$.

Technical grade sulfuric acid may be used in the process of this invention.

It is preferred that the aqueous sulfuric acid be employed in an amount of about 0.4 to 1.5 liters and more preferably from about 0.6 to 1.2 liters per kilogram of organopolysiloxanes, including for example fillers and all other substances other than the aqueous sulfuric acid used in the process of this invention.

It is preferred that the mixture of linear or branched organopolysiloxanes and aqueous sulfuric acid be heated to a temperature of from 130° to 150° C.

Since this is the least expensive, it is preferred that the process be carried out at atmospheric pressure, i.e. at 1 bar or at approximately 1 bar. Nevertheless, if desired, higher or lower pressures may be used as well.

Generally, the organopolysiloxanes and aqueous sulfuric acid are heated for from about 1.5 to 6 hours.

It is preferred that the mixture be stirred in order to ensure that the substances used in the process of this invention are thoroughly mixed.

The cyclic dimethylpolysiloxanes and water are recovered by distillation. Following the separation of the cyclic dimethylpolysiloxanes, the water can be recycled back in to the mixture of linear or branched organopolysiloxanes and aqueous sulfuric acid while ensuring that the concentration of sulfuric acid in the water does not exceed 80 percent by weight based on the total weight of sulfuric acid and water.

The process of this invention may be carried out batchwise or as semi-continuous or as a continuous process.

Although the sulfuric acid may be used repeatedly in the process of this invention, it is preferred that any solid residue be removed before it is used again in the process of this invention. When necessary, fresh sulfuric acid may be added as makeup.

Cyclic dimethylpolysiloxanes obtained in accordance with the process of this invention are neutral and need not be treated further or be further purified before they can be used, for example in the polymerization process to form, for example linear, highly viscous diorganopolysiloxanes which are subsequently used in the preparation of elastomers. Also they may be equilibrated with hexamethyldisiloxanes to form oils or fluid.

In the following example, all percentages are by weight unless otherwise specified.

EXAMPLE

The reaction is conducted in a vessel equipped with a stirrer and a vertical condenser which is connected to a separator which is adapted so that water collected in the bottom of the separator can be recycled to the vessel and the cyclic dimethylpolysiloxane can flow from the top of the separator. A mixture containing 400 g of a ground elastomer which was obtained by crosslinking a mixture consisting of 71.5 percent of linear highly viscous dimethylpolysiloxanes and 28.5 percent of pyrogenically produced silicon dioxide by means of an organic peroxide, and 500 ml of 65 percent aqueous sulfuric acid ($D^{20}=1.55$ g/cm$^3$) was heated with constant agitation to about 140° C. by means of a 185° C. oil bath. A mixture of cyclic dimethylpolysiloxanes and water is distilled off at a temperature of 95° to 97° C. Within 3 hours 253 g (89 percent of theoretical, based on the dimethylpolysiloxanes used) of cyclic dimethylpolysiloxanes are recovered from the separator. The dimethylpolysilocanes consist of 70 to 75 percent of octamethylcyclotetrasiloane and 15 to 20 percent of decamethylcyclopentasiloxane and mixtures of cyclic dimethylpolysiloxanes having varying degrees of polymerization.

What is claimed is:

1. A process for preparing cyclic dimethylpolysiloxanes which comprises heating a mixture containing linear or branched organopolysiloxanes having at least 50 mol percent of dimethylsiloxane units and an aqueous sulfuric acid in which the aqueous sulfuric acid contains from 50 to 85 percent by weight of sulfuric acid in the absence of an organic solvent while simultaneously distilling off the cyclic dimethylpolysiloxanes thus formed.

2. The process of claim 1, wherein the aqueous sulfuric acid contains from 55 to 80 percent by weight of sulfuric acid.

3. The process of claims 1 or 2, wherein from 0.4 to 1.5 liters of aqueous sulfuric acid are present per kilogram of mixture other than the aqueous sulfuric acid.

* * * * *